United States Patent [19]

Bishop et al.

[11] Patent Number: 5,204,447
[45] Date of Patent: Apr. 20, 1993

[54] PURIFICATION OF FACTOR XIII

[75] Inventors: Paul D. Bishop, Fall City; Gerald W. Lasser, Lynnwood, both of Wash.

[73] Assignee: ZymoGenetics, Inc., Seattle, Wash.

[21] Appl. No.: 270,714

[22] Filed: Nov. 14, 1988

[51] Int. Cl.$^5$ .......................... C07K 3/22; C07K 3/24; C07K 3/28; C07K 15/00

[52] U.S. Cl. .................................. 530/381; 530/380; 530/416; 530/417; 530/418; 530/419; 530/420; 530/421

[58] Field of Search ................ 424/105; 530/380, 381, 530/412, 416, 417, 418, 419, 420, 421; 435/69.6

[56] References Cited

U.S. PATENT DOCUMENTS 3,904,751 9/1975 Zwisler et al. .
3,931,399 1/1976 Bohn et al. .......................... 424/105

FOREIGN PATENT DOCUMENTS 69896 3/1987 Australia .
268772 6/1988 European Pat. Off. .

OTHER PUBLICATIONS

Calbiochem-Behring "Buffers—A Guide for the Preparation and use of Buffers in Biological Systems," (Gueffrog, D. E., ed.), (1983).
Ando et al. (1987) *J. Biochem* (Tokyo) 101(6) 1331-1338. Biol. Abstract 84:94751.
Buxman et al. (1976) *Biochim. Biophys. Acta.* 452, 356-369.
Scopes (1987) "Protein Purification: Principles and Practice" Springer-Verlag, New York, pp. 41-45, 33-37, & 50-54.
Lehninger (1970) "Biochemistry" 2nd ed., Worth Publishers, Inc., New York, pp. 157-163.
Pharmacia Separation News vol. 13-6, "A strategy for protein purification".
R. D. Cooke and J. J. Holbrook, *Biochem. J.* 141:79-84, 1974.
C. G. Curtis and L. Lorand, *Methods Enzymol.* 45:177-191, 1976.
A. G. Loewy et al., *J. Biol. Chem.* 236:2625, 1961.
J. McDonagh et al., *Biochim. Biophys. Acta* 446:345-357, 1976.
J. McDonagh et al., "Structure and Function of Factor XIII," in Colman et al. (eds.), *Hemostasis and Thrombosis*, J. B. Lipincott & Co., 1987, pp. 289-300.
S. Nakamura et al., *J. Biochem.* 78:1247-1266, 1975.

*Primary Examiner*—Robert A. Wax
*Assistant Examiner*—R. Keith Baker
*Attorney, Agent, or Firm*—Seed and Berry

[57] ABSTRACT

Methods for purifying factor XIII from a biological fluid are provided. The methods comprise precipitation of factor XIII by adjusting the pH of the biological fluid to 5.5 to 6.5 and recovering the precipitated factor XIII.

19 Claims, 2 Drawing Sheets

PURIFICATION OF FACTOR XIII

DESCRIPTION

1. Technical Field

The present invention relates to methods of protein purification in general, and more specifically to methods for purifying factor XIII from a variety of biological fluids.

2. Background of the Invention

Factor XIII (also known as fibrin stabilizing factor, fibrinoligase, or plasma transglutaminase) is a plasma glycoprotein that circulates in blood as a zymogen ($M_r = \sim 320$ kD) complexed with fibrinogen (Greenberg and Shuman, *J. Biol. Chem.* 257:6096–6101, 1982). Plasma factor XIII zymogen is a tetramer consisting of two a subunits ($M_r = \sim 75$ kD) and two b subunits ($M_r = \sim 80$ kD) (Chung et al., *J. Biol. Chem.* 249: 940–950, 1974) having an overall structure designated as $a_2b_2$. The a subunit contains the catalytic site of the enzyme, while the b subunit is thought to stabilize the a subunit or to regulate the activation of factor XIII (Folk and Finlayson, ibid.; Lorand et al., *Biochem. Biophys. Res. Comm.* 56:914–922, 1974). The amino acid sequences of the a and b subunits are known (Ichinose et al., *Biochemistry* 25:6900–6906, 1986; Ichinose et al., *Biochemistry* 25:4633–4638, 1986). Factor XIII occurs in placenta as an $a_2$ homodimer.

In vivo, activated factor XIII (factor XIIIa) catalyzes cross-linking reactions between other protein molecules. During the final stages of blood coagulation, thrombin converts factor XIII zymogen to an intermediate form ($a'_2b_2$), which then dissociates in the presence of calcium ions to produce factor XIIIa, a homodimer of a' subunits. Placental factor XIII is activated upon cleavage by thrombin. Factor XIIIa is a transglutaminase that catalyzes the cross-linking of fibrin polymers through the formation of intermolecular $\xi(\gamma$-glutamyl) lysine bonds, thereby increasing clot strength (Chen and Doolittle, *Proc. Natl. Acad. Sci. USA* 66:472–479, 1970; Pisano et al., *Ann. N.Y. Acad. Sci.* 202:98–113, 1972). This cross-linking reaction requires the presence of calcium ions (Lorand et al., *Prog. Hemost. Thromb.* 5:245–290, 1980; Folk and Finlayson, *Adv. Prot. Chem.* 31:1–133, 1977). Factor XIIIa also catalyzes the cross-linking of the γ chain of fibrin to $a_2$-plasmin inhibitor and fibronectin, as well as the cross-linking of collagen and fibronectin, which may be related to wound healing (Sakata and Aoki, *J. Clin. Invest.* 65:290–297, 1980; Mosher, *J. Biol. Chem.* 250:6614–6621, 1975; Mosher and Chad, *J. Clin. Invest.* 64:781–787, 1979; Folk and Finlayson, ibid.; Lorand et al., ibid.). The covalent incorporation of $a_2$-plasmin inhibitor into the fibrin network may increase the resistance of the clot to lysis (Lorand et al., ibid.).

Factor XIII deficiency results in "delayed bleeding," but does not affect primary hemostasis (Lorand et al., ibid). Current treatment practices for patients having factor XIII deficiencies generally involve replacement therapy with plasma or plasma derivatives, or with a crude placental factor XIII concentrate (Lorand et al., ibid.; Frobisch et al., *Dtsch. med. Wochenschr.* 97:449–502, 1972; Kuratsuji et al., *Haemostasis* 11:229–234, 1982).

Factor XIII is also useful in treatment of patients with disorders in postoperative wound healing (Mishima et al., *Chirurg* 55:803–808, 1984; Baer et al., *Zentrabl. Chir.* 105:642–651, 1980), scleroderma (Delbarre et al., *Lancet* 2:204, 1984; Guillevin et al., *La Presse Medicale* 14:2327–2329, 1985; Guillevin et al., *Pharmatherapeutica* 4:76–80, 1985; and Grivaux and Pieron, *Rev. Pnemol. Clin.* 43:102–103, 1987), ulcerative colitis (Suzuki and Takamura, *Thromb. Haemostas.* 58: 509, 1987), colitis pseudomembranous (Kuratsuji et al., *Haemostasis* 11:229–234, 1982) and as prophylactic of rebleeding in patients with subarachnoid hemorrhage (Henze et al., *Thromb. Haemostas.* 58:513, 1987). Furthermore, Factor XIII has been used as a component of tissue adhesives (U.S. Pat. Nos. 4,414,976; 4,453,939; 4,377,572; 4,362,567; 4,298,598; 4,265,233 and U.K. Patent No. GB 2 102 811 A).

A number of purification schemes for factor XIII have been described. Chung and Folk (*J. Biol. Chem.* 247:2798–2807, 1972) prepared factor XIII from platelet-concentrated plasma or from a fibrinogen preparation. Cooke and Holbrook (*Biochem. J.* 141:79–84, 1974) describe the purification of factor XIII from the Cohn-I fraction. The method involves multiple ammonium sulfate precipitation steps and fractionation on DEAE cellulose. Loewy et al. (*J. Biol. Chem.* 326:2625–2633, 1961) used ammonium sulfate fractionation and DEAE cellulose chromatography to purify factor XIII from plasma. Skrzynia et al. (*Blood* 60:1089–1095, 1985) purified the a subunit of factor XIII from a placental concentrate by chromatography and ammonium sulfate precipitation. Zwisler et al. (U.S. Pat. No. 3,904,751) and Bohn et al. (U.S. Pat. No. 3,931,399) describe multistep isolation procedures which rely on the use of diamino-ethoxy-acridine lactate to precipitate factor XIII. This precipitating agent would be an unacceptable contaminant in a therapeutic composition. Falke (U.S. Pat. No. 4,597,899) describes the isolation of factor XIII from an extract of placenta by alcohol precipitation.

Many of the previously described methods for purifying factor XIII have been directed to isolating it from plasma, serum, or fractions thereof. These starting materials are already enriched for factor XIII, and the contaminating proteins are generally well characterized and removable by known methods. Consequently, these purification schemes are poorly suited to preparing factor XIII from other, more heterogeneous starting materials, particularly crude cell lysates, where contaminating proteolytic activity may be high. Furthermore, many of these methods were developed for laboratory-scale purification and are difficult to scale up for economical preparation of therapeutic quantities of factor XIII.

There is therefore a need in the art for a simple, economical method for purifying factor XIII. Such a method should lend itself to large-scale production from crude starting materials, such as lysates of recombinant cells. The present invention provides such methods, together with other, related advantages.

DISCLOSURE OF THE INVENTION

The present invention provides a method for purifying factor XIII from a biological fluid, comprising adjusting the pH of the fluid to about pH 5.5 to 6.5 to precipitate the factor XIII, and subsequently recovering the precipitated factor XIII. The pH of the fluid is preferably adjusted by the use of a low ionic strength biological buffer, such as a heterocyclic polyamine or phosphate buffer. Suitable low ionic strength heterocyclic polyamines include piperazine, spermidine, cadaverine and derivatives thereof. In one embodiment, the factor XIII is precipitated by dialyzing the biological fluid in a buffer comprising 10-100 mM piperazine, pH 6.0.

A related aspect of the present invention provides a method for purifying factor XIII from a biological fluid, comprising the steps of (a) fractionating the biological fluid by anion exchange chromatography to produce an enriched fraction; (b) adjusting the pH of the enriched fraction to about pH 5.5 to 6.5 to precipitate the factor XIII; and (c) recovering the precipitated factor XIII.

This method may include the additional steps of dissolving the recovered, precipitated factor XIII to produce a solution, fractionating the solution by chromatography to produce a second enriched fraction, and recovering the second enriched fraction. In one embodiment, the biological fluid is a cleared cell lysate, such as a cleared yeast cell lysate. The biological fluid may be prepared by removing particulate material from a cell lysate to produce a cleared lysate, adding a precipitating agent to the cleared lysate to produce a precipitate, such as by adding ammonium sulfate to between about 30% and 40% of saturation or by adding polyethylene glycol to a concentration of between about 6% and 17% by weight, and resuspending the precipitate in a suitable buffer.

Other aspects of the invention will become evident upon reference to the following detailed description and attached drawings.

BEST MODE FOR CARRYING OUT THE INVENTION

Figure 1:
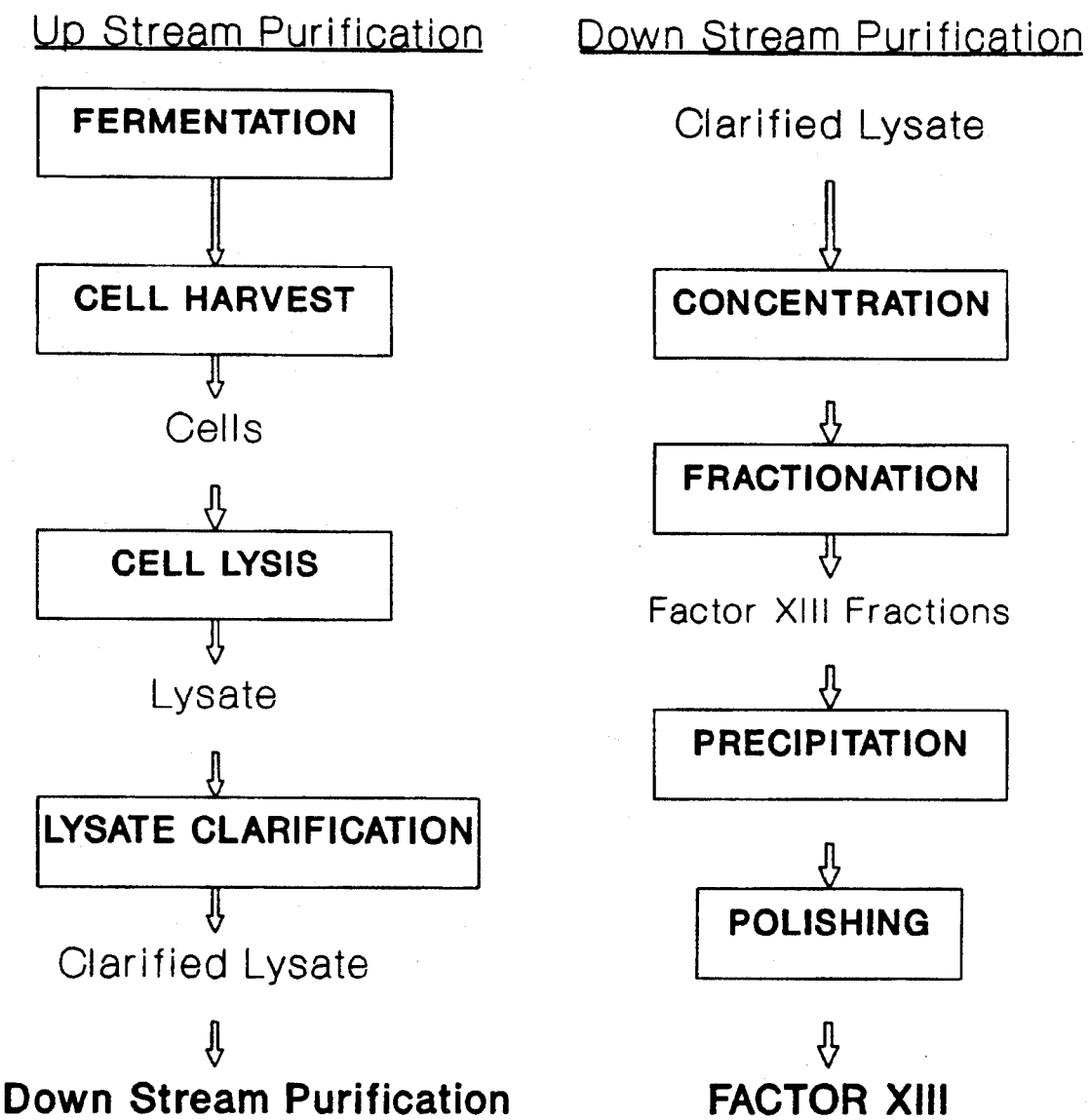
FIG. 1 is a flow chart summarizing the purification of recombinant factor XIII from yeast cells.

Prior to setting forth the invention, it may be beneficial for an understanding thereof to define certain terms used hereinafter.

Factor XIII: The term "factor XIII" includes the complete factor XIII zymogen tetramer, the $a'_2b_2$ intermediate and factor XIIIa, as well as subunits thereof, including the a subunit, the a' subunit and $a_2$ dimers.

Biological fluid: Any fluid derived from or containing cells, cell components or cell products. Biological fluids include, but are not limited to, cell culture supernatants, cell lysates, cleared cell lysates, cell extracts, tissue extracts, blood, plasma, serum, and fractions thereof.

Precipitating agent: A compound which, when added to a solution, causes another compound to precipitate from the solution. The precipitation may be due to the formation of a complex between the precipitating agent and the other compound or a phase change resulting in insolubility. Precipitating agents include organic modifiers e.g., ethanol, propanol, polyethylene glycol, and salts, such as ammonium sulfate.

Buffer: A substance that prevents appreciable changes of pH in solutions to which small amounts of acids or bases are added. A buffer generally comprises a combination of the proton-donor and proton-acceptor forms of a weak acid or weak base. Addition of small amounts of acid or base to a buffered solution shifts the equilibrium between the proton donor and proton acceptor. This equilibrium shift stabilizes the pH.

The present invention provides methods of purifying factor XIII from a variety of biological fluids. Suitable biological fluids include lysates or extracts of cells which naturally produce factor XIII in recoverable amounts, such as placental cells, as well as blood and blood fractions. Lysates and extracts of such cells and tissues may be prepared by a variety of procedures known in the art. However, due to the risk of viral contamination of blood and tissues, fluids derived from virus-free cells or cell lines which have been genetically modified to produce factor XIII are preferred sources. Particularly preferred biological fluids in this regard include lysates and cleared lysates of yeast cells which have been transformed to produce factor XIII, although in principle, any cell type capable of expressing cloned DNA sequences may be used.

Within the present invention, it has been found that factor XIII is insoluble in low ionic strength solutions having a pH at or about its isoelectric point (i.e., approximately 5.8), allowing separation of factor XIII from a solution without the need for precipitating agents. Thus, according to the present invention, factor XIII is isolated from a biological fluid by adjusting the pH of the fluid to about pH 5.5 to 6.5, such as by buffer exchange, to form a precipitate. The precipitate may be further purified prior to use or may be used directly, such as in the preparation of tissue adhesives. Preferred buffers for precipitation include low ionic strength solutions of heterocyclic polyamines, such as piperazine, spermidine, cadaverine and derivatives thereof adjusted to the desired pH. Piperazine and piperazine derivatives, such as piperazine sulfate, are particularly preferred. Other suitable buffers include biological buffers having a useful pH range around pH 6.0, including MES, phosphate, ADA and Bis-Tris. Buffers will generally be used at a concentration of between about 10 mM and 100 mM, preferably about 50 mM. Buffers may be obtained from commercial suppliers such as Sigma Chemical Co., St. Louis, Mo. As used herein, the term "low ionic strength" includes solutions having a conductance of less than about 150 mS (equivalent to about 200 mM NaCl).

As noted above, recombinant cells and cell lines are preferred sources of factor XIII. Production of factor XIII in recombinant cells, including bacteria, yeast and cultured mammalian cells, has been described by Grundmann et al. (published Australian patent application 69896/87) and Davie et al. (U.S. Ser. No. 174,287; EP 268,772), which are incorporated herein by reference. Methods for expressing cloned DNA sequences are well known in the art. Briefly, a DNA sequence encoding factor XIII is operably linked to suitable promoter and terminator sequences, and this expression unit is inserted into a vector compatible with the chosen host cell. The vector is then inserted into the host cell and the resulting recombinant cells are cultured to produce factor XIII. Depending on the particular host cell and the expression unit utilized, the factor XIII may either be secreted from the cell or retained in the cytoplasm.

When using cells which do not secrete the factor XIII, the cells are removed from the culture medium (e.g., by centrifugation) and treated to produce a lysate. Typically, yeast cells are treated by mechanical disruption using glass beads to produce a crude lysate. Preferably, the crude lysate is centrifuged at low speed (e.g., 2,000×g) and the supernatant fraction is recovered. Streptomycin sulfate (2%) is added and the supernatant is treated to produce a cleared lysate, typically by high-speed centrifugation (e.g., 20,000–30,000×g). The resulting cleared lysate may then be enriched and fractionated prior to precipitating the factor XIII by buffer exchange. Suitable methods of enrichment include treating the cleared lysate by the addition of ammonium sulfate to about 30%–40%, preferably about 35% of saturation, or by the addition of polyethylene glycol to about 6% to 17%, preferably about 6%–12%, by weight. The mixture is then incubated for about 30 minutes to 3 hours to produce a precipitate. In one embodiment, pharmaceutical grade polyethylene glycol (molecular weight of 4000 to 8000) is added to 8% by weight, and the solution is incubated at 4° C. for one hour. As will be apparent to one of ordinary skill in the art, time, temperature and concentration of precipitating agent are interrelated and can be varied accordingly. The resulting precipitate is then recovered, typically by centrifugation, and resuspended in a low ionic strength, mildly alkaline buffer. It is preferred that the buffer contain a protease inhibitor, such as phenyl methyl sulfonyl fluoride (PMSF), leupeptin or pepstatin. A particularly preferred buffer in this regard is 50 mM Tris-HCl, pH 7.5 containing 5 mM Na$_2$EDTA, 5 mM 2-mercaptoethanol and 0.5 mM PMSF. When using ammonium sulfate precipitation, it will be necessary to reduce the salt concentration in the resuspended precipitate, such as by dialysis, prior to further purification. The resulting biological fluid is then fractionated as set forth below.

Factor XIII may also be obtained from cells which secrete it into the culture medium. Generally, the cells are removed by centrifugation and the medium is fractionated as described below. Alternatively, the culture medium may be enriched for factor XIII, such as by the precipitation procedure described above, and the resuspended precipitate subsequently fractionated.

When working with biological fluids containing complex mixtures of proteins it will generally be preferred to fractionate the biological fluid by anion exchange chromatography to produce an enriched fraction. Factor XIII is then precipitated from the resulting enriched fraction by buffer exchange. Typically, the biological fluid is passed over a column of an anion exchange medium and eluted using a shallow salt gradient in a buffer at least about 0.5 pH units lower than the loading buffer. A preferred elution protocol utilizes a gradient of 0–150 mM NaCl in 50 mM imidazole, pH 6.3. Suitable anion exchange media include derivatized Sephadex (Pharmacia, Piscataway, N.J.), cellulose, polyacrylamide, specialty silicas, etc. PEI, DEAE and QAE derivatives are preferred, with DEAE fast-flow Sephadex being particularly preferred. As will be appreciated by those skilled in the art, fractionation can also be carried out in a batch process. Peak fractions are pooled for subsequent purification of the factor XIII. It is generally preferred at this stage to reduce the volume of the pooled fractions by concentration. A preferred method of concentration is precipitation of the factor XIII with 70% saturated (NH$_4$)$_2$SO$_4$.

Factor XIII is then precipitated by adjusting the pH of the factor XIII preparation as described above. In a preferred embodiment, an enriched fraction, prepared by ammonium sulfate precipitation as disclosed above, is dissolved in 50 mM piperazine, pH adjusted to 6.0 with HCl, containing 5 mM EDTA, 5 mM 2-mercaptoethanol (2-ME), 0.02% NaN$_3$ at 4° C. and dialyzed against the same buffer for five hours at 4° C. to produce a precipitate. The precipitate is recovered by centrifugation and washed several times in fresh piperazine buffer. At this point, the factor XIII preparation is typically about 98% pure. Precipitation of factor XIII from other biological fluids will be carried out in substantially the same manner, i.e., by dialyzing the fluid against the precipitation buffer to produce a precipitate.

Additional purification may be obtained by dissolving the precipitated factor XIII in a low ionic strength buffer at about pH 7.4–8.0, such as 50 mM Tris, pH 7.5, 50 mM NaCl, or 50 mM glycine, pH 7.5, 50 mM NaCl, and repeating the step of precipitation at pH 5.5–6.5. This preparation is then recovered and resuspended in a suitable buffer to be used directly or further purified as described below.

If desired, final purification is achieved through the use of conventional chemical separation techniques, including ion exchange chromatography, size-exclusion chromatography, etc. In many instances it will be desirable to remove residual proteases from the preparation. In one embodiment, this is achieved by dissolving the precipitated factor XIII to produce a solution, typically in a low ionic strength buffer at slightly alkaline pH, such as 50 mM Tris, pH 8.0 or 50 mM Imidazole, pH 8.0 containing 200 mM NaCl, then fractionating the solution by size exclusion chromatography. Suitable chromatographic media in this regard include cross-linked dextran, polyacrylamide and specialty silicas with hydrophilic coatings or bonded phases. Sephadex S-200 (Pharmacia) is a particularly preferred dextran-based medium. In a preferred embodiment, the piperazine precipitate is redissolved in 50 mM Tris-HCl, pH 8.0, 200 mM NaCl, 2.5 mM EDTA, 1 mM 2-mercaptoethanol. The solution is centrifuged to remove any insoluble residue, and the supernatant is fractionated on a Sephadex S-200 column. Peak fractions are pooled and dialyzed against an appropriate storage buffer. Factor XIII prepared in this way is typically greater than 99% pure and pyrogen-free.

Factor XIII prepared by the methods described herein may be used to produce pharmaceutical preparations, such as tissue adhesives, according to methods known in the art. Such preparations are described in, for example, U.S. Pat. No. 4,265,233 and published Australian Patent Application 75097/87, herein incorporated by reference.

The following examples are offered by way of illustration and not by way of limitation.

EXAMPLES

Example 1: Purification of Factor XIII Using Piperazine Buffer

A. Fermentation and Up-Stream Processing

An exemplary method for purifying factor XIII from recombinant yeast cells is summarized in FIG. 1. Briefly, the cells are harvested, lysed, and the lysate is clarified. The clarified lysate is then concentrated and fractionated by chromatography. Factor XIII is precipitated from the factor XIII-containing fractions using piperazine, and a final polishing step is used to remove trace contaminants.

*Saccharomyces cerevisiae* strain ZMI118 (a MATa/MATα diploid homozygous for leu2-3,112 ura3 tpil::URA3+ bar1 pep4::URA3+ [cir°]) was transformed with a vector (designated pD16) containing an expression unit for the factor XIII a-subunit. The transformed cells were inoculated at approximately 0.1 g/l and cultured in a pH 5.5 medium containing 25 g/l yeast extract, 22.5 g/l $(NH_4)_2SO_4$, 6.5 g/l $KH_2PO_4$, 3 g/l $MgSO_4$ and 0.5% glucose with a glucose feed from 0 to 24 or 40 hours and an ethanol feed from 0 to 12 or 20 hours. The cultures (10 to 60 liters) were grown at 30° C. to a final cell density of approximately 60 g/l.

Cell cultures were harvested by concentration using a 0.2μ cellulose ester hollow fiber cartridge (Microgon, Laguna Hills, Calif.). The final concentrate typically contained 600–3000 g wet weight of yeast cells (concentration >50% wet weight) in deionized $H_2O$.

The concentrated cells were then lysed. A maximum of 400 g (wet weight) of cells was diluted to 40% wet weight in lysis buffer (50 mM Tris HCl, pH 7.4, 150 mM NaCl, 15 mM EDTA, 5 mM 2-ME, 1 mM PMSF). The cells were lysed using a Dynomill (Glen Mills, Inc., Maywood, N.J.) in continuous flow mode. The cell suspension was combined with 0.5 liter of acid-washed 500μ glass beads in a 0.6 liter container and lysed at 3000 rpm using a flow rate of 60–100 ml/min. to give an average residence time of 3–5 minutes. An additional one liter of buffer was pumped through the container.

The lysate was then clarified by centrifugation. One-liter bottles of lysate were centrifuged in a Sorvall RC-3B centrifuge at 5000 rpm in an H-6000A rotor for 45 minutes and the pellets were discarded. The supernatant fractions were then conditioned by the addition of PMSF to a final concentration of 1 mM and 0.3 volume of 7% streptomycin sulfate. The mixture was then allowed to stand for 12 hours at 4° C. Final clarification was achieved by centrifugation in a Sorvall RC-5B centrifuge using 500 ml bottles in a GS-3 rotor at 7500 rpm for 90 minutes and/or 250 ml bottles in a GSA rotor at 12,000 rpm for 60 minutes. The resulting clarified lysate was then ready for down-stream processing.

B. Down-Stream Processing

The clarified lysate was fractionated by the addition of polyethylene glycol 1000 (PEG-1000) to a final concentration of 12% or PEG-8000 to a concentration of 8%. The mixture was incubated at 4° C. for 1 hour, then centrifuged using 500 ml bottles in a Sorvall GS-3 rotor at 7500 rpm for 90 minutes and/or 250 ml bottles in a GSA rotor at 12,000 rpm for 60 minutes. The precipitate was recovered.

Figure 2:
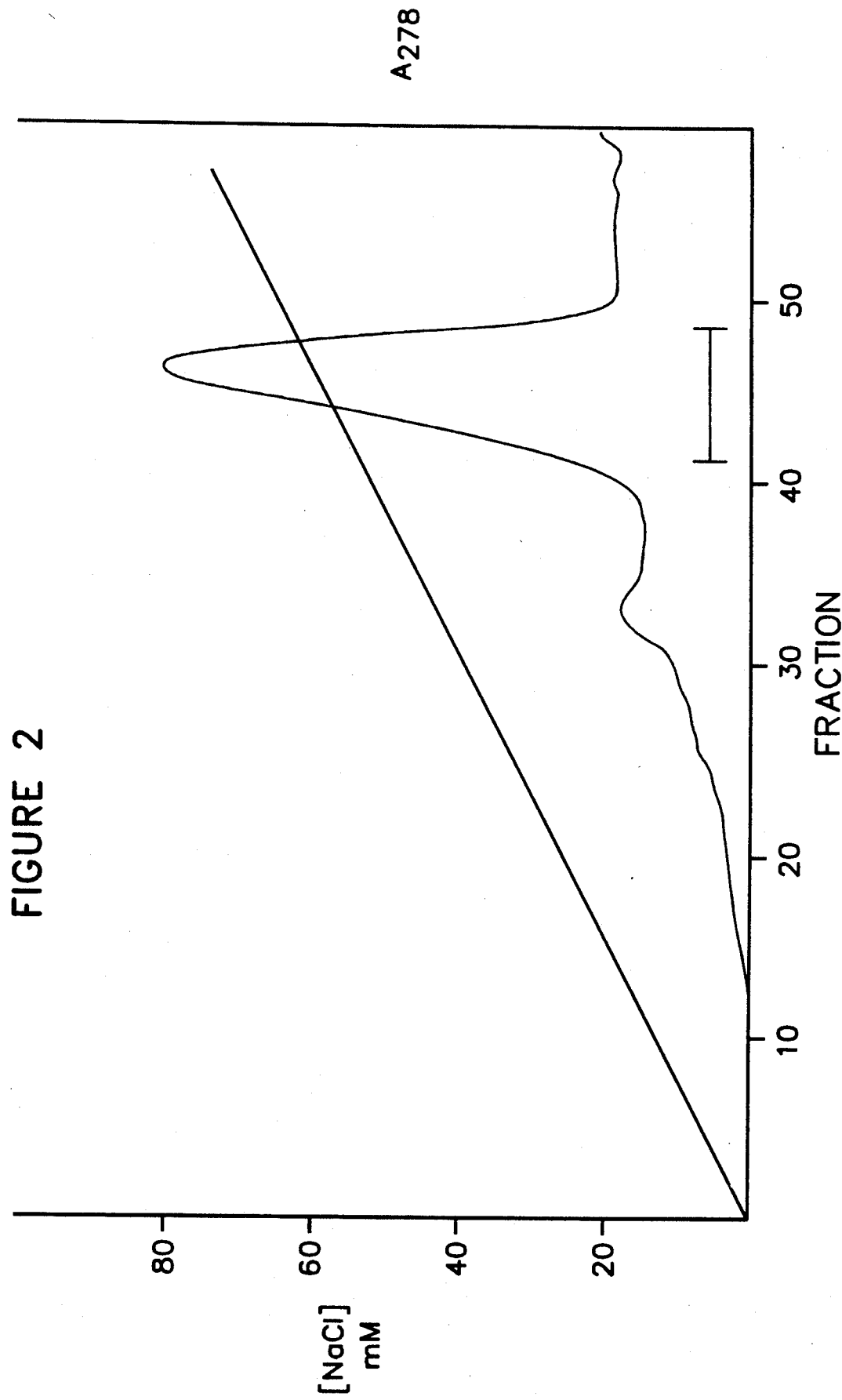
FIG. 2 illustrates a typical elution profile of factor XIII from DEAE fast-flow Sephadex. The bar indicates the fractions which were pooled for subsequent piperazine precipitation.

The PEG precipitate was dissolved in starting buffer (50 mM Tris-HCl, pH 7.8, 5 mM EDTA, 5 mM 2-ME, 0.5 mM PMSF) and the resulting solution was loaded on a 6×27 cm (500 ml) column of DEAE fast-flow Sephadex (Pharmacia). The column was washed with 1 l of starting buffer, and the factor XIII was eluted using a linear gradient of 1 l each of buffer A (50 mM imidazole, pH 6.3, 5 mM EDTA, 5 mM 2-ME) and buffer B (buffer A containing 150 mM NaCl). A typical elution profile is illustrated in FIG. 2. Fractions were assayed by measuring the incorporation of $^3H$-histamine into N,N-dimethyl casein or by enzyme-linked immunosorbent assay. Pooled Factor XIII-containing fractions were precipitated by addition of $(NH_4)_2SO_4$ to 70% of saturation.

Factor XIII was then precipitated using piperazine buffer. The $(NH_4)_2SO_4$ mixture was centrifuged and the supernatant fraction was discarded. The pellet was dissolved in 50 mM Tris, pH 8.0, 200 mM NaCl, 2.5 mM EDTA, 1 mM 2-ME and dialyzed in 50 mM piperazine, pH 6.0, 5 mM EDTA, 5 mM 2-ME, 0.02% $NaN_3$ at 4° C. for about 5–12 hours. The mixture was then centrifuged at 5000 rpm for five minutes in a Sorvall RC-5B centrifuge using an SS-34 rotor. The resulting pellet was washed several times in fresh piperazine buffer.

Final purification was achieved by gel filtration. The piperazine pellet was resuspended in running buffer (50 mM Tris HCl, pH 8.0, 200 mM NaCl, 2.5 mM EDTA, 1 mM 2-ME) at a concentration of <100 mg precipitate per 20 ml buffer. The solution was dialyzed in running buffer for 5 hours at 4° C. and centrifuged to remove any residue. The dialyzed solution was then loaded onto a 4.5×80 cm (1270 ml) Sephadex S-200 column. The column was eluted with running buffer at 0.17 ml/minute. Factor XIII peak fractions were pooled.

Table 1 summarizes the purification steps described above. Yields were determined by a sandwich enzyme-linked immunosorbent assay (ELISA) using a mouse monoclonal antibody to placental factor XIII and a rabbit polyclonal antibody. Yields may be underestimated. Activity was determined by $^3H$-histamine incorporation.

TABLE 1

| | Total Protein (g) | Total Activity (cpm × $10^{-9}$) | Specific Activity (cpm/g × $10^{-9}$) | Step Yield (%) | Overall Yield (%) |
|---|---|---|---|---|---|
| Crude Lysate | 65 | 85 | 1.3 | 100 | 100 |
| Clarified Lysate | 34 | 91 | 2.7 | 107 | 107 |
| PEG ppt | 5.6 | 52 | 9.2 | 57 | 61 |
| DEAE (pH jump) | 0.72 | 26 | 37 | 50 | 31 |
| Piperazine ppt | 0.31 | 47 | 150 | 138 | 55 |
| S-200 | | | 168 | >68 | 37 |

Crude Lysate by ELISA ... 480 mg total FXIII
Total Yield at Piperazine ppt ... 65%

Example 2: Precipitation of Factor XIII

Factor XIII, purified as described above, was dissolved in 50 mM Tris-HCl, pH 8.0, 200 mM NaCl, 2.5 mM EDTA, 1 mM 2-ME at a concentration of approximately 5.8 mg/ml. 0.5 ml aliquots of the resulting solution were pipetted into dialysis bags and dialyzed for two days at 4° C. in the following buffers:

50 mM MES (2-[N-Morpholino] ethanesulfonic acid), pH 6.1
50 mM PIP (Piperazine), pH 6.2
50 mM phosphate, pH 6.0
50 mM ADA (N-[2-Acetamido]-2-iminodiacetic acid), pH 6.0
50 mM Bis-Tris (bis[2-Hydroxyethyl]-imino-tris[hydroxymethyl] methane), pH 6.1
Buffers were obtained from Sigma Chemical Co., St. Louis, Mo.

Following dialysis, the contents of the dialysis bags were centrifuged and the pellets and supernatants were assayed for factor XIII by the Bradford method using Protein Assay Reagent 23200 (Pierce Chemical Co.) as described by the manufacturer. The results, summarized in Table 2, indicate that factor XIII is insoluble in a variety of buffers at or about its isoelectric point.

TABLE 2

| Buffer | Gain in Volume (ml) | Absorbance (595 nm) Super | ppt | Concentration (mg/ml) Super | ppt |
|---|---|---|---|---|---|
| MES | .30 | .29 | .48 | .38 | .61 |
| PIP | −.10 | .22 | .26 | .28 | .33 |
| Phosphate | .50 | .25 | .50 | .31 | .64 |
| ADA | .20 | .33 | .49 | .41 | .62 |
| Bis-Tris | .30 | .23 | .49 | .29 | .62 |

Although the foregoing invention has been described in some detail by way of illustration and example for purposes of clarity of understanding, it will be evident that certain changes and modifications may be practiced within the scope of the appended claims.

We claim:

1. A method for purifying factor XIII from a biological fluid, comprising:
   precipitating the factor XIII by adjusting the pH of the biological fluid to 5.5 to 6.5; and
   recovering the precipitated factor XIII.

2. The method of claim 1 wherein the pH of the fluid is adjusted by the use of a low ionic strength, polyamine or phosphate buffer.

3. The method of claim 2 wherein the low ionic strength polyamine is selected from the group consisting of piperazine and derivatives thereof.

4. The method of claim 1 wherein the precipitating step comprises dialyzing the biological fluid in a buffer comprising 10–100 mM piperazine, pH 6.0.

5. The method of claim 1, further comprising washing the recovered, precipitated factor XIII.

6. A method for purifying factor XIII from a biological fluid, comprising:
   fractioning the biological fluid by anion exchange chromatography to produce an enriched fraction;
   precipitating the factor XIII by adjusting the pH of the enriched fraction to 5.5 to 6.5; and
   recovering the precipitated factor XIII.

7. The method of claim 6, comprising the additional steps of:
   dissolving the recovered, precipitated factor XIII to produce a solution;
   fractionating the solution by chromatography to produce a second enriched fraction; and
   recovering the second enriched fraction.

8. The method of claim 6 wherein the pH of the enriched fraction is adjusted by the use of a low ionic strength, polyamine or phosphate buffer.

9. The method of claim 8 wherein the low ionic strength polyamine is selected from the group consisting of piperazine and derivatives thereof.

10. The method of claim 6 wherein the precipitating step comprises dialyzing the enriched fraction in a buffer comprising 10–100 mM piperazine, pH 6.0.

11. The method of claim 6 wherein the biological fluid is a cleared cell lysate.

12. The method of claim 11 wherein the cleared cell lysate is a yeast cell lysate.

13. The method of claim 6 wherein the biological fluid is prepared from a cell lysate by:
   removing particulate material from a cell lysate to produce a cleared lysate;
   adding a precipitating agent to the cleared lysate to produce a precipitate; and
   resuspending the precipitate in a suitable buffer to form a biological fluid.

14. The method of claim 13 wherein the step of adding a precipitating agent comprises adding ammonium sulfate to between about 30% to 40% of saturation, or adding polyethylene glycol to a concentration of between about 6% to 17% by weight.

15. The method of claim 6 wherein the fractionating step comprises chromatography on DEAE anion exchange media.

16. The method of claim 7 wherein the step of fractionating the solution by chromatography comprises filtration of the solution on gel filtration chromatography media.

17. A method for purifying factor XIII from a biological fluid, comprising:
   adding to a biological fluid ammonium sulfate to about 30% to about 40% of saturation to produce a precipitate;
   resuspending the precipitate in a low ionic strength, mildly alkaline buffer;
   fractioning the resuspended precipitate by anion exchange chromatography to produce an enriched fraction;
   precipitating the factor XIII by adjusting the pH of the enriched fraction to 5.5 to 6.5 with piperazine buffer;
   recovering the precipitated factor XIII;
   dissolving the precipitated factor XIII to produce a solution;
   fractioning the solution by size exclusion chromatography to produce a second enriched fraction; and
   recovering the second enriched fraction.

18. The method of claim 17 wherein the biological fluid is a cleared cell lysate.

19. The method of claim 18 wherein the cleared cell lysate is a yeast cell lysate.

* * * * *